(12) United States Patent
Glasnapp

(10) Patent No.: US 10,342,849 B2
(45) Date of Patent: *Jul. 9, 2019

(54) ANTIBIOTIC COMPOSITION COMPRISING A CHEMOTACTIC AGENT AND A NUTRIENT DISPERSION

(71) Applicant: Professional Compounding Centers of America (PCCA), Houston, TX (US)

(72) Inventor: Andrew B. Glasnapp, Sugar Land, TX (US)

(73) Assignee: Professional Compounding Centers of America (PCCA), Houston, TX (US)

(*) Notice: Subject to any disclaimer, the term of this patent is extended or adjusted under 35 U.S.C. 154(b) by 29 days.

This patent is subject to a terminal disclaimer.

(21) Appl. No.: 15/179,402

(22) Filed: Jun. 10, 2016

(65) Prior Publication Data

US 2016/0279191 A1 Sep. 29, 2016

Related U.S. Application Data

(63) Continuation of application No. 13/899,980, filed on May 22, 2013, now Pat. No. 9,387,189.

(51) Int. Cl.

| | |
|---|---|
| *A23L 5/00* | (2016.01) |
| *A61K 38/06* | (2006.01) |
| *A61K 38/12* | (2006.01) |
| *A61K 38/17* | (2006.01) |
| *A61K 38/19* | (2006.01) |
| *A61K 38/20* | (2006.01) |
| *A61K 45/06* | (2006.01) |
| *A61K 47/10* | (2017.01) |
| *A61K 47/12* | (2006.01) |
| *A61K 47/18* | (2017.01) |
| *A61K 47/26* | (2006.01) |
| *A61K 47/34* | (2017.01) |
| *A61K 47/42* | (2017.01) |
| *A61L 27/16* | (2006.01) |
| *A61L 27/52* | (2006.01) |
| *A61L 27/54* | (2006.01) |
| *A61K 31/202* | (2006.01) |
| *A61K 31/351* | (2006.01) |
| *A61K 31/496* | (2006.01) |
| *A61K 31/5383* | (2006.01) |
| *A61K 31/7036* | (2006.01) |

(52) U.S. Cl.
CPC .......... *A61K 38/12* (2013.01); *A23L 5/00* (2016.08); *A61K 31/202* (2013.01); *A61K 31/351* (2013.01); *A61K 31/496* (2013.01); *A61K 31/5383* (2013.01); *A61K 31/7036* (2013.01); *A61K 38/06* (2013.01); *A61K 38/1725* (2013.01); *A61K 38/195* (2013.01); *A61K 38/2053* (2013.01); *A61K 45/06* (2013.01); *A61K 47/10* (2013.01); *A61K 47/12* (2013.01); *A61K 47/183* (2013.01); *A61K 47/26* (2013.01); *A61K 47/34* (2013.01); *A61K 47/42* (2013.01); *A61L 27/16* (2013.01); *A61L 27/52* (2013.01); *A61L 27/54* (2013.01); *A61L 2430/00* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 5,700,444 A | * 12/1997 | Zamora | A61K 49/14 424/1.11 |
| 7,955,818 B2 | 6/2011 | Bernardi et al. | |
| 9,387,189 B2 | * 7/2016 | Glasnapp | A61K 31/202 |
| 2007/0202051 A1 | * 8/2007 | Schuschnig | A61K 9/0043 424/45 |
| 2008/0249022 A1 | 10/2008 | Grote et al. | |
| 2009/0117109 A1 | 5/2009 | Thornthwaite et al. | |
| 2009/0232744 A1 | 9/2009 | Keller et al. | |

(Continued)

OTHER PUBLICATIONS

Ross et al (Journal of Aerosol Medicine and Pulmonary Drug Delivery, (Apr. 2013) vol. 26, No. 2, pp. A29-A30. Abstract No. P-028. Abstract presented at 19th International Congress of the International Society for Aerosols in Medicine. Chapel Hill, NC, United States; Apr. 6-10, 2013) (Year: 2013).*
Patel et al (International Journal of PharmTech Research; vol. 1, No. 2, pp. 299-303 , Apr.-Jun. 2009) (Year: 2009).*
Graff, Jason R et al. "Vibrio Cholerae Exploits Sub-Lethal Concentrations of a Competitor-Produced Antibiotic to Avoid Toxic Interactions." Frontiers in microbiology 4 (2013).

(Continued)

*Primary Examiner* — Brian Gangle
*Assistant Examiner* — Andrea K McCollum
(74) *Attorney, Agent, or Firm* — David G. Woodral; GableGotwals

(57) ABSTRACT

Compositions and methods for treating infectious diseases produced by biofilms are disclosed. More specifically, the present disclosure refers to a pharmaceutical composition which may be used for treating biofilm infections, specifically, biofilms formed by bacteria such as *Pseudomonas, E. coli, Klebsiella*, and other human pathogens. Pharmaceutical compositions may include a nutrient dispersion that can include sodium citrate, succinic acid, xylitol, glutamic acid, and ethylenediaminetetraacetic acid (EDTA), among others. Additionally disclosed pharmaceutical composition may include active pharmaceutical ingredients (API) such as antibiotics. Subsequently, the antibiotics agent may be ciprofloxacin, amikacin, tobramycin, colistin methate, or polymixin, among others. Pharmaceutical compositions disclosed may employ chemotactic agents in order to disrupt biofilms and therefore enhance the antibiotic response. Pharmaceutical compositions disclosed may include suitable vehicles which may depend on the dosage form.

10 Claims, 1 Drawing Sheet

(56) References Cited

U.S. PATENT DOCUMENTS

2011/0039763 A1  2/2011  Eckert et al.
2011/0218139 A1  9/2011  Robinson et al.
2012/0321687 A1  12/2012  Hughes et al.

OTHER PUBLICATIONS

Sommerfeld Ross, et al. "Nutrient Dispersion Enhances Conventional Antibiotic Activity Against . . . " Int'l Journal of Antimicrobial Agents 40.2 (2012): 177-181. NCBI PubMed. Web.

* cited by examiner

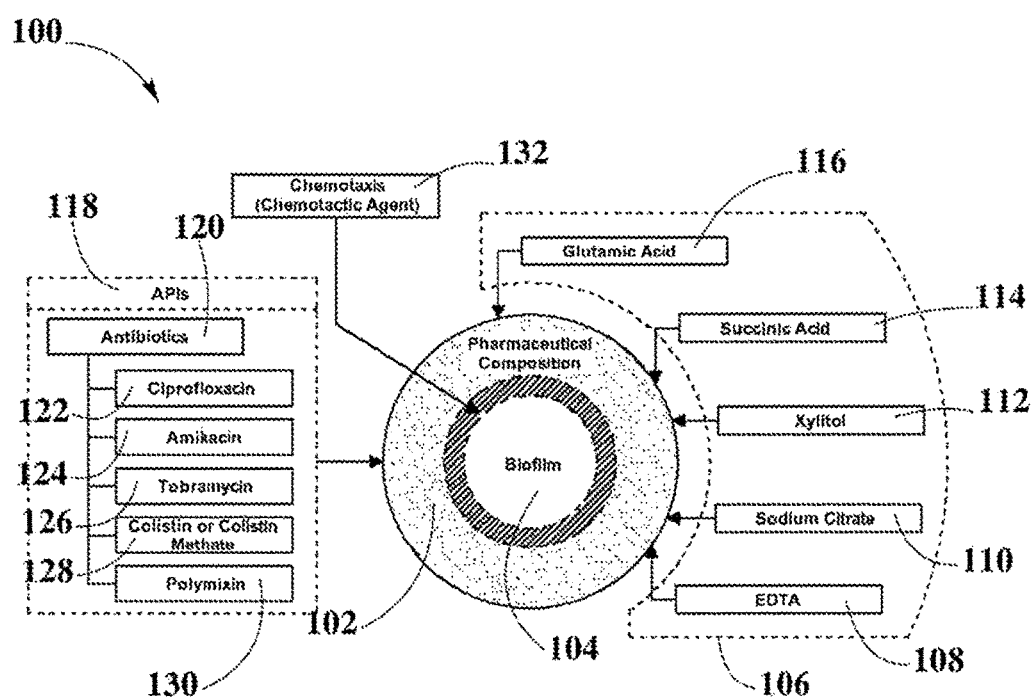

ANTIBIOTIC COMPOSITION COMPRISING A CHEMOTACTIC AGENT AND A NUTRIENT DISPERSION

CROSS-REFERENCE TO RELATED CASES

This is a continuation of co-pending U.S. patent application Ser. No. 13/899,980, entitled "AN ANTIBIOTIC COMPOSITION COMPRISING A CHEMOTACTIC AGENT AND A NUTRIENT DISPERSION" filed on May 22, 2013, the contents of which are hereby incorporated by reference.

FIELD OF THE INVENTION

The present disclosure relates generally to microbial infections, and more particularly, to methods and compositions for treating bacterial biofilm using pharmaceutical compositions.

BACKGROUND OF THE INVENTION

Bacterial biofilms cause significant infections in the medical field. Antibiotics commonly used to treat these infections often do not achieve complete bacterial eradication. New approaches to eliminate biofilms have focused on dispersion compounds to entice the bacteria to actively escape or disperse from the biofilm, where the bacteria may become more susceptible to antibiotics.

Current researches have identified the genes that may be specifically involved in increased resistance of biofilm cells, where there has been isolated several mutants of uropathogenic *Eserichia coli*, and *Staphylococcus aureus* and which form "normal" biofilms, but which do not possess increased resistance. The persistence of, for example, staphylococcal infections related to foreign bodies is due to biofilm formation. Likewise, chronic *Pseudomonas aeruginosa* lung infection in cystic fibrosis patients is caused by biofilm-growing mucoid strains. Furthermore, biofilm growth is associated with an increased level of mutations as well as with quorum-sensing-regulated mechanisms.

Characteristically, gradients of nutrients and oxygen exist from the top to the bottom of biofilms and these gradients are associated with decreased bacterial metabolic activity and increased doubling times of the bacterial cells; it is these more or less dormant cells that are responsible for some of the tolerance to antibiotics. Biofilms may be prevented by early aggressive antibiotic prophylaxis or therapy and may be treated by chronic suppressive therapy.

Moreover, a term that may be commonly used for chronic diseases as consequence of bacterial biofilms is bacterial chemotaxis. Specifically, chemotaxis may be described as the directed cell locomotion in concentration gradients of soluble extracellular agents. Substances that induce a chemotactic response (chemotactic factors) are known also under the general name of cytotaxin, chemotaxin, or chemoattractants. Additionally, cells showing positive chemotaxis move towards areas with higher concentrations of chemotactic agents, while those showing negative chemotaxis moves away from these areas.

Numerous active pharmaceutical ingredients (APIs) such as antibiotics in combination with chemotactic agents have been studied in order to produce a pharmaceutical composition that could be effective in disrupting bacterial biofilms. However, there is no specific research that could provide a suitable dosage or concentration of antibiotics, chemotactic agent, or any other chemical agent to kill or eradicate the biofilms in different sites of human body.

There is therefore a need for pharmaceutical compositions that may include chemotactic agents combined with APIs, such as antibiotics, and other ingredients that could be effective for disrupting bacterial biofilms or microbial colonies. Therefore, various dosage forms of the pharmaceutical composition that include chemotactic agents may be used for treating some chronic diseases.

SUMMARY OF THE INVENTION

According to various embodiments, the present disclosure relates to compositions and methods for treating infectious diseases produced by biofilms. More specifically, the present disclosure refers to a pharmaceutical composition that may be administrated in dosage form such as mouth rinses, nasal sprays, solutions, oral solutions, inhalation solution, oral liquids suspensions, and capsules, among others. The pharmaceutical compositions may be used for disrupting bacterial biofilms, specifically, biofilms formed by bacteria such as *Pseudomonas, E. coli, Klebsiella*, and other human pathogens.

According to one embodiment, the pharmaceutical composition may be used for disrupting biofilms formed in chronic infections such as bacterial vaginosis, chronic nasal and sinus infections (sinusitis, chronic rhinosinusitis), oral and dental infections (periodontal diseases such as chronic periodontitis), cystic fibrosis, and chronic gangrene (by infection or ischemia), among others.

According to one embodiment, the pharmaceutical composition may include a nutrient dispersion that may include compounds such as, sodium citrate, succinic acid, xylitol, glutamic acid, and ethylenediaminetetraacetic acid (EDTA). In addition, the pharmaceutical composition may include APIs such as antibiotic agents.

Some embodiments may include antibiotic agents such as ciprofloxacin, amikacin, tobramycin, colistin methate, and polymixin, among others. Specifically, the pharmaceutical composition may include about 1 mM to about 100 mM of sodium citrate, most suitable may be about 10 mM of sodium citrate; about 7.5 mM to about 300 mM of xylitol, most suitable may be 75 mM of xylitol; about 1 mM to about 100 mM of glutamic acid, most suitable may be 10 mM of glutamic acid; about 0.1% by weight to about 10% by weight of EDTA, and about 0.1% by weight to about 5.0% by weight of ciprofloxacin (antibiotic).

In one embodiment, the pharmaceutical composition may include about 0.1% by weight to about 5.0% by weight of tobramycin as antibiotic agent. In further embodiments, the pharmaceutical composition may include about 0.1% by weight to about 5.0% by weight of colistin methate as antibiotic agent. In still further embodiments, the pharmaceutical composition may include 0.1% by weight to about 5.0% by weight of polymixin as antibiotic agent.

In one embodiment, the pharmaceutical composition may include suitable vehicles which may depend on the dosage form, where suitable vehicle ingredients may be poloxamers, water, propylene glycol, polyethylene glycol, fatty acids, methylcellulose, oils, starch, petroleum derivatives such as mineral oil and white petrolatum, lactose, gums, microcrystalline cellulose, and silicones, among others.

Pharmaceutical compositions may be used for disrupting bacterial biofilms via chemotaxis because pharmaceutical compositions may include chemotactic agents that may enhance the antibiotics activity. The chemotactic agents may be used as an energy source in a solution around the microbes (biofilm), subsequently, the microbes may change the proteins that they secrete. Consequently, the microbes may disrupt their own biofilm and move through the energy source, exposing themselves to the API (such as antibiotics) within the pharmaceutical composition.

Numerous other aspects, features and advantages of the present disclosure may be made apparent from the following detailed description taken together with the drawing FIGURES.

BRIEF DESCRIPTION OF THE DRAWINGS

The present disclosure can be better understood by referring to the following FIGURES. The components in the FIGURES are not necessarily to scale, emphasis instead being placed upon illustrating the principles of the invention. In the figures, reference numerals designate corresponding parts throughout the different views.

FIG. 1 depicts a block diagram of a pharmaceutical composition for disrupting bacterial biofilms, according to an embodiment.

DETAILED DESCRIPTION OF THE PREFERRED EMBODIMENTS

The present disclosure is herein described in detail with reference to embodiments illustrated in the drawings, which form a part here. In the drawings, which are not necessarily to scale or to proportion, similar symbols typically identify similar components, unless context dictates otherwise. Other embodiments may be used and/or other changes may be made without departing from the spirit or scope of the present disclosure. The illustrative embodiments described in the detailed description are not meant to be limiting of the subject matter presented herein.

As used here, the following terms may have the following definitions:

"Chemotaxis" refers to the characteristic movement or orientation of an organism/microorganism or cell along a chemical concentration gradient either toward or away from a chemical stimulus.

"Biofilm" refers to a structured consortium of bacteria embedded in a self-produced polymer matrix consisting of polysaccharides, protein and DNA.

"Active pharmaceutical ingredient" or "API" refers to a chemical compound that induces a desired pharmacological, physiological effect, and include agents that are therapeutically effective, prophylactically effective, or cosmetically effective.

"Treating" and "treatment" refers to a reduction in severity and/or frequency of symptoms, elimination of symptoms and/or underlying cause, prevention of the occurrence of symptoms and/or their underlying cause, and improvement or remediation of damage.

"Nutrient dispersion" refers to a dispersion of compounds that entice bacteria to actively escape or disrupt from the biofilm, where the bacteria may become more susceptible to antibiotics.

FIG. 1 depicts block diagram 100 of pharmaceutical composition 102 for disrupting bacterial biofilm 104, according to an embodiment. More specifically, the pharmaceutical composition 102 may be used for disrupting biofilms 104 formed in chronic infections such as bacterial vaginosis, chronic nasal and sinus infections (sinusitis, chronic rhinosinusitis), oral and dental infections (periodontal diseases such as chronic periodontitis), cystic fibrosis, and chronic gangrene (by infection or ischemia), among others.

According to one embodiment, a pharmaceutical composition 102 may include nutrient dispersion 106 that includes compounds such as, sodium citrate 110, succinic acid 114, xylitol 112, glutamic acid 116, and EDTA 108. In addition, pharmaceutical compositions 102 may include APIs 118 such as antibiotic 120 agents. Some embodiments may include antibiotic 120 agents such as ciprofloxacin 122, amikacin 124, tobramycin 126, colistin methate 128, and polymixin 130, among others.

More specifically, pharmaceutical composition 102 may include about 1 mM to about 100 mM of sodium citrate 110, most suitable may be about 10 mM of sodium citrate 110; about 7.5 mM to about 300 mM of xylitol 112, most suitable may be 75 mM of xylitol 112; about 1.0 mM to about 100 mM of glutamic acid 116, most suitable may be 10 mM of glutamic acid 116; about 0.1% by weight to about 10% by weight of EDTA 108, and about 0.1% by weight to about 5.0% by weight of ciprofloxacin 122 (as an antibiotic 120 agent).

In one embodiment, pharmaceutical composition 102 may include about 0.1% by weight to about 5.0% by weight of tobramycin 126 as antibiotic 120 agent. In further embodiments, pharmaceutical composition 102 may include about 0.1% by weight to about 5.0% by weight of colistin methate 128 as antibiotic 120 agent. In still further embodiments, pharmaceutical composition 102 may include 0.1% by weight to about 5.0% by weight of polymixin 130 as antibiotic 120 agent.

In one embodiment, a pharmaceutical compositions 102 may include suitable vehicles which may depend on the dosage form, where suitable vehicles ingredients may be poloxamers, water, propylene glycol, polyethylene glycol, fatty acids, methylcellulose, oils, starch, petroleum derivatives such as mineral oil and white petrolatum, lactose, gums, microcrystalline cellulose, and silicones, among others.

Furthermore, a pharmaceutical composition 102 may disrupt bacterial biofilms 104 via chemotaxis because pharmaceutical compositions 102 may include chemotactic agents 132 in order to enhance antibiotics 120 activity. According to some embodiments, chemotactic agents 132 may be used as energy source in a solution around the bacteria within biofilm 104, such that, bacteria may change the proteins that they secrete. Consequently, the bacteria may disrupt their own biofilm 104 and move through the energy source, exposing themselves to a pharmaceutical composition 102 which may include antibiotics 120.

Chemotactic agents 132 may include for instance small proteins with a terminal formyl group, such as fMLP (N-formyl-Methionyl-Leucyl-Phenylalanine). Other chemotactic agents 132 may be activated complement factors (such as the anaphyloxins C3a and C5a), leukotrienes (such as Leukotriene B4 (LTB4) and Platelet-Activating Factor (PAF)); another group may be the chemokines produced by different cell types such as interleukin-8 (monocytes and endothelial cells), chemokine ligand 5 (CCL5 or also known as regulated upon activation normal T-cell expressed and secreted (RANTES)), eotaxin, monocyte chemotactic protein (MCP), and macrophage inflammatory protein (MIP), among others.

Antibiotic Agents

According to some embodiments antibiotic 120 agents may include: ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin g, penicillin v, piperacillin tazobactam, ticarcillin clavulanic acid, nafcillin, cephalosporin i generation antibiotics, cefadroxil, cefazolin, cephalexin, cephalothin, cephapirin, cephradine cefactor, cefamandol, cefonicid, cefotetan, cefoxitin, cefprozil, ceftmetazole, cefuroxime, loracarbef, cefdinir, ceftibuten, cefoperazone, cefixime, cefotaxime, cefpodoxime proxetil, ceftazidime, ceftizoxime, ceftriaxone, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, mozzxifloxacin, nalidixic acid, norfloxacin, ofloxacin, sparfloxacin, trovafloxacin, oxolinic acid, gemifloxacin, perfloxacin, imipenem-cilastatin, meropenem, aztreonam, amikacin, gentamicin, kanamycin, neomycin, netilmicin, streptomycin, tobramycin, paromomycin, teicoplanin, vancomycin, demeclocycline, doxycycline, methacycline, minocycline, oxytetracycline, tetracycline, chlortetracycline, mafenide, silver sulfadiazine, sulfacetamide, sulfadiazine, sulfamethoxazole, sulfasalazine, sulfisoxazole, trimethoprim-sulfamethoxazole, sulfamethizole, rifabutin, rifampin, rifapentine, linezolid, streptogramins, quinopristin dalfopristin, bacitracin, chloramphenicol, fosfomycin, isoniazid, methenamine, metronidazol, mupirocin, nitrofurantoin, nitrofurazone, novobiocin, polymyxin, spectinomycin, trimethoprim, colistin, cycloserine, capreomycin, ethionamide, pyrazinamide, para-aminosalicyclic acid, erythromycin ethylsuccinate and combinations thereof.

Administration Route of the Pharmaceutical Composition

The most suitable route of pharmaceutical composition 102 may depend on the nature and severity of the condition being treated. In one embodiment, pharmaceutical composition 102 may be administered in dosage form such as mouth rinses, nasal sprays, solutions, oral solutions, inhalation solution, gels, oral liquids suspensions, ointments, creams, ointments, anhydrous solutions, lotions, and capsules, among others. A pharmaceutical composition 102 may be used for disrupting biofilms 104 infections, specifically, in biofilms 104 formed by bacteria such as *Pseudomonas, E. coli, Klebsiella*, and other human pathogens. In an embodiment, the pharmaceutical composition can be administered to an animal, which can be a mammal. In an embodiment, a mammal is human.

In another embodiment, a pharmaceutical composition 102 may be administered and manufactured by any suitable means known in the art, for example, topically (including via direct application to skin or to any epithelial tissue surface, including such surfaces as may be present in glandular tissues or in the respiratory and/or gastrointestinal tracts), vaginally, intraperitoneally, orally, parenterally, intravenously, intraarterially, transdermally, sublingually, subcutaneously, intramuscularly, transbuccally, intranasally, via inhalation, intraoccularly, subcutaneously, intraadiposally, and intraarticularly or intrathecally among others.

For instance, in topical administration the carrier may include a solution, emulsion, ointment or gel base. The base, for example, may include one or more components such as petrolatum, lanolin, polyethylene glycols, bee wax, mineral oil, diluents such as water and alcohol, and emulsifiers and stabilizers, among others.

According to some embodiments, topical administration may include direct application into an opened wound. For instance, an opened fracture or another opened wound may include a break in the skin that may expose additional underlying tissues to the external environment in a manner that renders them susceptible to microbial infection.

In one embodiment, topical formulation may be provided in the forms of a cream, lotion, solution, spray, gel, ointment, paste, micelles, microspheres and other microparticle/nanoparticle delivery elements, among others.

EXAMPLES

Example #1 is an application of a pharmaceutical composition 102, which may be used for disrupting a bacterial biofilm 104 in animals. Pharmaceutical compositions 102 for animals may be in any suitable dosage form such as mouth rinses, nasal sprays, solutions, oral solutions, inhalation solution, topical gels, creams, oral liquids suspensions, and capsules, among others.

Example #2 is an embodiment of pharmaceutical composition 102, which may include APIs 118 such as antibiotics 120 and antifungals.

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. An anti-biofilm composition, comprising:
   a chemotactic agent;
   a nutrient dispersion including sodium citrate, xylitol, and glutamic acid; and
   an antibiotic.

2. The anti-biofilm composition of claim 1, wherein the chemotactic agent comprises a protein with a terminal formyl group.

3. The anti-biofilm composition of claim 1, wherein the chemotactic agent is N-formyl-Methionyl-Leucyl-Phenylalanine.

4. The anti-biofilm composition of claim 1, wherein the chemotactic agent is an activated complement factor.

5. The anti-biofilm composition of claim 1, wherein the chemotactic agent is chemokine.

6. The anti-biofilm composition of claim 1, wherein the chemotactic agent is a monocyte chemotactic protein (MCP).

7. The anti-biofilm composition of claim 1, wherein the chemotactic agent is a macrophage inflammatory protein (MIP).

8. The anti-biofilm composition of claim 2, wherein the nutrient dispersion comprises about 1 mM to about 100 mM of sodium citrate, about 7.5 mM to about 300 mM of xylitol, and about 1.0 mM to about 100 mM of glutamic acid.

9. The anti-biofilm composition of claim 1, further comprising a poloxamer.

10. The anti-biofilm composition of claim 1, wherein the antibiotic is selected from the group consisting of bacitracin, polymixin, mupirocin, neomycin, tobramycin, colistin methate, gentamicin, and levofloxacin.

\* \* \* \* \*